United States Patent [19]

Reilly et al.

[11] Patent Number: 4,963,607
[45] Date of Patent: Oct. 16, 1990

[54] COMPOSITIONS AND METHODS USING ORGANOSULFIDES FOR STABILIZATION OF POLYOLEFINS AGAINST PHOTODEGRADATION

[75] Inventors: James L. Reilly, Towamencin; Joseph M. Bohen, King of Prussia, both of Pa.

[73] Assignee: Pennwalt Corporation, Philadelphia, Pa.

[21] Appl. No.: 366,311

[22] Filed: Jun. 13, 1989

Related U.S. Application Data

[63] Continuation of Ser. No. 220,875, Jul. 15, 1988, abandoned, which is a continuation of Ser. No. 924,104, Oct. 31, 1986, abandoned, which is a continuation of Ser. No. 659,486, Oct. 10, 1984, abandoned.

[51] Int. Cl.$^5$ ................................................ C08K 5/36
[52] U.S. Cl. .................................... 524/291; 524/296; 524/336; 524/337; 524/338; 524/367; 524/368; 524/392
[58] Field of Search .............. 524/338, 367, 368, 392, 524/336, 337, 291, 296; 568/39, 57, 58

[56] References Cited

U.S. PATENT DOCUMENTS

| | | | |
|---|---|---|---|
| T.985,004 | 8/1979 | Paul | 260/45.75 |
| 2,967,848 | 1/1961 | Hawkins et al. | 524/392 |
| 2,972,597 | 2/1961 | Newland | 524/336 |
| 2,995,539 | 8/1961 | Barker | 524/368 |
| 3,010,937 | 11/1961 | Roos et al. | 524/392 |
| 3,033,814 | 5/1962 | Tholstrup | 524/291 |
| 3,122,519 | 2/1964 | Baum | 524/392 |
| 3,223,738 | 12/1965 | Crain et al. | 524/392 |
| 3,258,493 | 6/1966 | Braus et al. | 524/392 |
| 3,293,209 | 12/1966 | Baldwin et al. | 524/392 |
| 3,301,816 | 1/1967 | Burgess | 524/336 |
| 3,313,772 | 4/1967 | Moss et al. | 524/304 |
| 3,322,705 | 5/1967 | Kauder | 524/147 |
| 3,370,036 | 2/1968 | Martinovich | 524/299 |
| 3,392,141 | 7/1968 | Blumberg et al. | 524/392 |
| 3,409,594 | 11/1968 | Slovinsky | 528/336 |
| 3,440,212 | 4/1969 | Tholstrup | 524/291 |
| 3,445,424 | 5/1969 | Martinovich | 524/336 |
| 3,536,661 | 10/1970 | Hagemeyer et al. | 524/289 |
| 3,538,044 | 11/1970 | Buchholz et al. | 524/333 |
| 3,549,588 | 12/1970 | Kopacki et al. | 524/91 |
| 3,642,690 | 2/1972 | Mills | 524/100 |
| 3,645,963 | 2/1972 | Kopacki et al. | 524/392 |
| 3,652,680 | 3/1972 | Buchholz | 568/57 |
| 3,716,586 | 2/1973 | Hofer et al. | 568/43 |
| 3,772,246 | 11/1973 | Buchholz | 524/392 |
| 3,839,277 | 10/1974 | Spivack et al. | 524/291 |
| 3,935,163 | 1/1976 | Spivack et al. | 524/91 |
| 3,935,164 | 1/1976 | Spivack et al. | 524/91 |
| 4,025,582 | 5/1977 | Needham | 525/189 |
| 4,185,297 | 2/1980 | Jayne et al. | 252/406 |

FOREIGN PATENT DOCUMENTS

| | | |
|---|---|---|
| 725507 | 10/1965 | Canada . |
| 1265409 | 4/1968 | Fed. Rep. of Germany . |
| 1694210 | 4/1971 | Fed. Rep. of Germany . |
| 41-16184 | 9/1966 | Japan . |
| 43-21415 | 9/1968 | Japan . |
| 50-105740 | 8/1975 | Japan . |
| 966929 | 8/1964 | United Kingdom . |
| 981346 | 1/1965 | United Kingdom . |
| 1015797 | 1/1966 | United Kingdom . |

OTHER PUBLICATIONS

David MacNicol et al.: *Tetrahedron Letters*, No. 34, p. 2969–2972 (1977).

Khirud B. Chakraborty et al: European Polymer Journal–vol. 13, pp. 1007 to 1013 (1977).

Norman Neureiter et al; Industrial & Engineering Chemistry Product Res. & Dev., vol. 1, No. 4, pp. 236–241 (1962).

Derwent Japanese Patents Report 5, No. 37, p 1:6 (10-17-66).

David D. MacNichol and Stephen Swanson "Synthesis and Inclusion Properties of Twelve–Membered Carbocyclic Hosts" Tetrahedron Letters, No. 34, pp. 2969–2972 (1977) Pergamon Press.

*Primary Examiner*—Veronica P. Hoke
*Attorney, Agent, or Firm*—Bernard F. Plantz

[57] ABSTRACT

Polyolefins are stabilized against the harmful effects of U.V.-light by incorporating therein certain organosulfides. The organosulfides may be used alone or in synergistic combination with two classes of known light stabilizers, namely the benzophenones and the esters of aromatic acids.

32 Claims, No Drawings

COMPOSITIONS AND METHODS USING ORGANOSULFIDES FOR STABILIZATION OF POLYOLEFINS AGAINST PHOTODEGRADATION

This application is a continuation of application Ser. No. 07/220,875 filed July 15, 1988, now abandoned which is a continuation of application Ser. No. 06/924,104 filed Oct. 31, 1986, now abandoned, which is a continuation of application Ser. No. 06/659,486 filed Oct. 10, 1984, now abandoned.

The present invention relates to compositions and methods for stabilizing polymeric materials against the detrimental effects produced by exposure to actinic radiation, such as visible or U.V.-light rays. This invention is particularly concerned with preventing U.V.-light-induced degradation of polyolefin resin, especially polyethylene and polypropylene, by incorporating therein certain organosulfide compounds, either alone or in synergistic combination with certain aromatic ketones or aromatic acid esters. Also within the scope of this invention is a novel class of U.V.-light stabilizer organosulfide compounds.

Polyolefin resins, such as polyethylene and polypropylene, have long been used in the manufacture of foils, films, fibers and molded articles. Because of their excellent structural properties, e.g. tensile strength, dimensional stability, etc., the manufactured materials have been extensively used in the construction trades. When used outdoors, however, these materials are continuously exposed to sunlight and U.V.-radiation, which causes severe deterioration of the polyolefin resin, as evidenced by surface cracking, loss of tensile strength and discoloration.

A number of so-called U.V.-light stabilizers are known which inhibit the deleterious effects of actinic radiation on various organic resins and plastics. Among the commercially available U.V.-light stabilizers for polyolefin resins are aromatic acid esters and ketones, especially salicylates, and benzophenones. These U.V.-light stabilizers function by a screening process, absorbing the harmful U.V. radiation and dissipating the energy as heat. Generally speaking, however, it is extremely difficult to predict whether a given substance will be effective as a U.V.-light stabilizer for polyolefin resins, since stabilizers which have been effective for other resins or plastics are often insufficiently compatible with polyolefin resins for practical utilization therein. Thus, some otherwise useful stabilizers have a tendency to exude from polyolefin resins after incorporation, or to evaporate during processing or thereafter, in either case leaving the resin inadequately protected against photodegradation.

Certain sulfur-containing organic substances are disclosed in the prior art as U.V.-light stabilizers for polyolefin resins. For example, U.S. Pat. No. 3,645,963 discloses that poly(alkylenesulfide) protects polyolefins from the adverse effects of U.V.-light. The poly(alkylenesulfide) is composed of monomeric units having from 2 to 4 carbon atoms in either a straight or a branched chain. U.S. Pat. No. 4,025,582 discloses the addition of poly(phenylenesulfide) to a polyolefin resin for stabilization against U.V.-light. However, as far as is known, neither of these polysulfides has been used commercially to any significant extent.

It is also known that one can enhance the effectiveness of certain U.V.-light stabilizers by using a synergist in conjunction therewith. However, merely because a substance functions as a U.V.-light stabilizer synergist, it does not necessarily follow that the substance has any significant U.V.-light stabilizing activity on its own. For example, U.S. Pat. No. 2,972,597 discloses the stabilization of poly-α-olefin compositions against U.V.-light induced degradation using a diester of $\beta,\beta'$-thiodipropionic acid in combination with a certain group of benzophenone compounds. It is disclosed that the combination exhibits synergy. However, experience has shown that diesters of thiodipiopionic acid such as dilauryl thiodipropionate (DLTDP) and distearyl thiodipropionate (DSTDP), when used alone, exhibit little, if any, U.V.-light stabilizing activity. Indeed, the use of such commercial organosulfide synergists may actually impair the effectiveness of certain U.V.-light stabilizer compounds. For this reason, organosulfides are generally not used in light stabilized polyolefin resin compositions. Also, in U.S. Pat. No. 3,322,705 it is disclosed that polyolefins may be stabilized against photodegradation using a three-component mixture comprising a 2-hydroxy-4-benzyloxy-benzophenone, a thiodipropionate and a metal salt of a monocarboxylic acid. It is also mentioned in that patent that synergistic activity is observed when such benzophenones are used in combination with sulfur-containing compounds, which are described as including organic mercaptans and organic polysulfides.

The use of organosulfides, either alone or in combination with a benzophenone or an aromatic acid ester, for polyolefin resin stabilization, according to the present invention, is to be distinguished from the use of sulfur-containing organic compounds as additives for stabilizing organic resins against other potentially harmful agents. It is known, for example, to use sulfur-containing organic compounds as synergists for inhibition of oxidative degradation of organic resins, which is often caused during processing, e.g. by rolling, injection molding, extrusion and the like, at elevated temperatures. U.S. Pat. Nos. 3,652,680 and 3,772,246 which are commonly owned with the present application, relate to cycloalkane bis(alkylsulfides) and the use thereof as antioxidant synergists. Other sulfur containing organic compounds commonly used as antioxidant synergists are diesters of thiodialkanoic acid, and especially DSTDP and DLTDP. See, for example, Neureiter et al., *Synergism Between Phenol and Sulfides in the Stabilization of Polyolefins to Oxidation*, I & EC Product Research and Development, Vol. 1, No. 4 p. 236 (1962). U.S. Pat. Nos. 3,440,212 and 3,033,814 also disclose the use of dialkylthiodipropionates in a synergistic three-component mixture with certain bisphenols and phenyl salicylates to achieve protection against thermal oxidation of polyolefins.

Another known sulfur-containing organic compound having utility as an antioxidant in polymer stabilization is 4,4'-thiobis-(3-methyl-6-t-butyl phenol). Use of this antioxidant, in combination with certain known U.V.-light stabilizer compounds, is disclosed in U.S. Pat. No. 3,370,036.

U.S. Pat. No. 3,301,816 discloses the use of mercaptols, mercaptals, orthothioesters, orthothiocarbonates, and alkylidene and aralkylidene polymeric mercaptols and mercaptals as heat stabilizers, in conjunction with known U.V.-light stabilizers. Additional sulfur-containing compounds said to have utility in the stabilization of polyolefins to heat-induced oxidation are disclosed in U.S. Pat. Nos. 3,392,141 (polycyclohexylene disulfides), 3,010,937 (thioacetals), and 2,967,848 (aliphatic mercaptans).

From the foregoing, it can be seen that prior disclosures relating to the use of organosulfides for inhibiting photodegradation of polyolefin resin have been rather narrow in scope, with only a small number of specific substances identified as being effective for this purpose.

SUMMARY OF THE INVENTION

It has now been discovered, in accordance with the present invention, that a reasonably broad class of organosulfides, when incorporated in a polyolefin resin in combination with either a benzophenone or an aromatic acid ester, produce a synergistic light stabilizing effect. In addition, these organosulfides have unexpectedly been found to significantly improve stability of polyolefins to photodegradation, when used alone.

Thus, in one aspect, the present invention provides compositions comprising certain benzophenones or aromatic acid esters, known to have U.V.-light stabilizing activity, and a synergizing amount of an organosulfide.

According to another aspect of the present invention, there is provided a method for stabilizing polyolefin resin against degradation by sun light or U.V.-radiation which comprises incorporating in the polyolefin resin an effective amount of the aforesaid U.V.-light stabilizing composition.

The present invention further encompasses certain polymeric compositions of matter comprising polyolefin resin, particularly polyethylene and polypropylene, stabilized with the aforesaid U.V.-light stabilizing composition.

Also within the scope of the present invention is a method of stabilizing polyolefin resin against photodegradation using a subgroup of the aforementioned class of organosulfides.

According to another aspect of this invention there is provided a novel class of organosulfide compounds that stabilize polyolefins against U.V. light.

The organosulfides utilized in the present invention display excellent compatibility with and retention in a wide variety of polyolefin resins.

DETAILED DESCRIPTION

The U.V.-light stabilizing compositions for polyolefins comprise in combination:

a. a benzophenone having U.V.-light stabilizing activity or an aromatic ester having U.V.-light stabilizing activity, or a mixture thereof; and b. a synergizing amount of an organosulfide of the formula:

$$(R_1X_1)_m\text{—}[R_2\text{—}X_2]_n\text{—}R_3$$

wherein $R_1$ and $R_3$ may be the same or different and are independently selected from the group of hydrogen, alkyl having 1 to 30 carbon atoms, cycloalkyl having 3 to 20 carbon atoms, cycloalkylalkyl having 4 to 20 carbon atoms, and aryl having 6 to 20 carbon atoms, which radicals may optionally be substituted with substituents from the group of halogen or —YR, wherein Y is either oxygen or sulfur and R is a hydrocarbon radical from the group of alkyl having 1 to 20 carbon atoms, alkenyl having 2 to 20 carbon atoms, cycloalkyl having 3 to 20 carbon atoms, aryl having 6 to 20 carbon atoms or alkaryl having 7 to 20 carbon atoms;

m represents a number from 1 to 10;

$R_2$ represents a linking group selected from the group of straight or branched, saturated or unsaturated aliphatic having 1 to 20 carbon atoms, alicyclic having 3 to 20 carbon atoms, alicyclicalkyl having 4 to 20 carbon atoms, or aromatic having 6 to 20 carbon atoms, or a plurality of said linking groups, which may be the same or different, and which are joined by oxygen or sulfur, said linking groups being optionally substituted with substituents from the group of halogen or —YR, wherein Y and R are as defined above;

$X_1$ and $X_2$ represent oxygen or sulfur, at least one of said $X_1$ and $X_2$ being sulfur; and n is a number from 0 to 1,000, but when n is 0, $R_1$ and $R_3$ are not the same and neither $R_1$ nor $R_3$ is hydrogen.

The substituted groups $R_1$ and $R_3$ are preferably non-aromatic and unsubstituted.

Representative organosulfides falling within the above formula are:

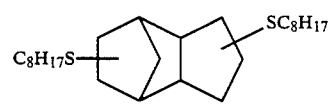

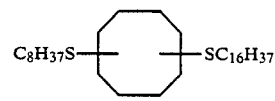

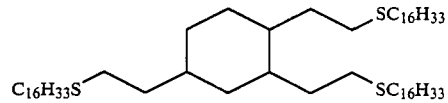

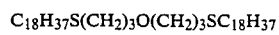

$C_{18}H_{37}S(CH_2)_3O(CH_2)_3SC_{18}H_{37}$ $C_{16}H_{33}S(CH_2)_{10}SC_{16}H_{33}$

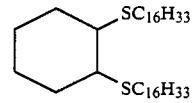

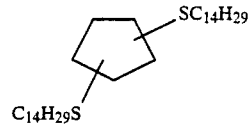

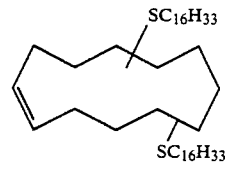

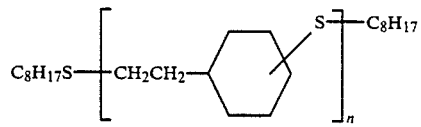

$HS\text{—}[(CH_2)_4S(CH_2)_{10}S]_n\text{—}H$

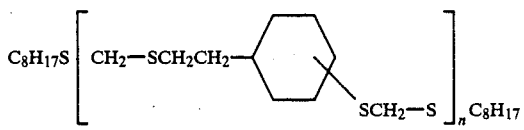

Preferred organosulfides are those wherein $R_1$ and $R_3$ in the above general formula may be the same or different and are independently selected from the group of hydrogen or alkyl having 8 to 30 carbon atoms;

m represents a number from 1 to 5;

$R_2$ represents a linking group selected from the group of alicyclic having 5 to 15 carbon atoms;

$X_1$ and $X_2$ represent sulfur; and n is 1.

Some examples of the preferred organosulfides include:

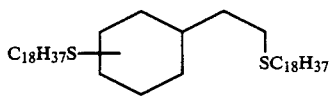

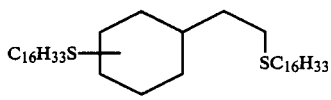

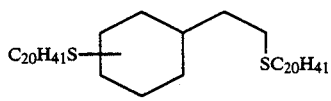

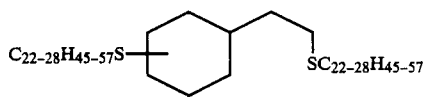

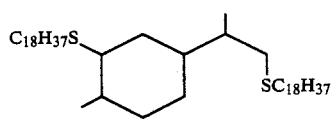

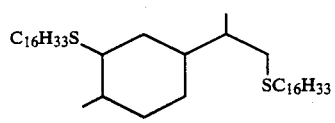

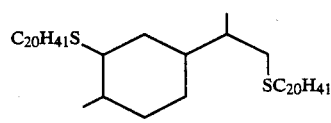

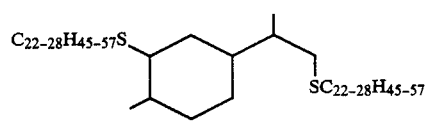

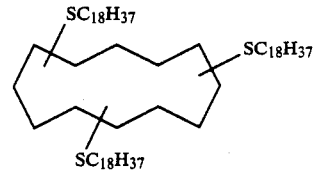

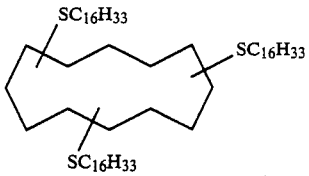

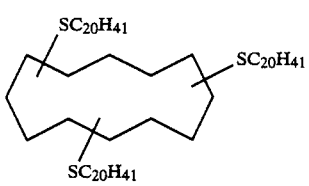

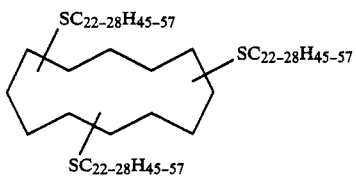

Another organosulfide within the above general formula that has been particularly effective as a U.V.-light stabilizer synergist is:

$$HO\text{-}[CH_2CH_2S]_n\text{-}H$$

The expression "independently selected from", when used herein in reference to multiple repeating substituents, e.g. $(R_1X_1)_m$, where m is greater than one, signifies that each time the substituent in question appears in a particular organosulfide, it may or may not be the same.

As previously noted, one aspect of the present invention is directed to a novel class of organosulfide compounds having utility as U.V.-radiation stabilizers. These compounds have the formula:

$$(R_1SCH)_x \quad (CH_2)_y$$

wherein $R_1$ is independently selected from the group of hydrogen or alkyl having 1 to 30 carbon atoms, cycloalkyl having 3 to 20 carbon atoms, and aryl having 6 to 20 carbon atoms, which radicals may optionally be substituted with substituents from the group of halogen or —YR, wherein Y and R are as defined above;

x is from 2 to 6;

y is from 6 to 14; and provided that x+y is at least 8 and no more than 16.

The organosulfides of this invention can be conveniently prepared by the reaction of a diene, triene, etc., with a mercaptan as described in the aforementioned U.S. Pat. Nos. 3,772,246 and 3,652,680; or by the reaction of a mono olefin with a di-, tri- or higher substituted mercaptan. These reactions are illustrated as follows:

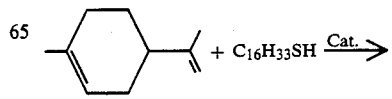

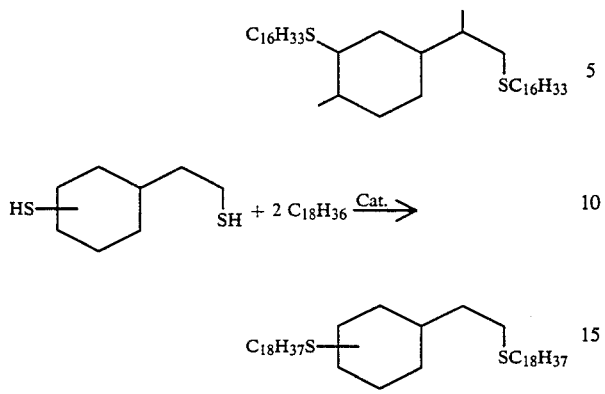

The above reactions occur in the presence of conventional free radical catalysts such as ultraviolet light, gamma radiation, peroxides and azo compounds.

The organosulfur compounds utilized in this invention can also be prepared by the reaction of a mercaptan or a salt of a mercaptan with a hydrocarbon containing a suitable leaving group, such as halogen, hydroxyl, or the like, as described in U.S. Pat. No. 3,293,209, and illustrated as follows:

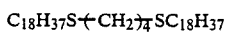

The polymeric organosulfides used in the practice of this invention may be prepared according to the following polycondensation reaction, as generally described in U.S. Pat. No. 3,317,486:

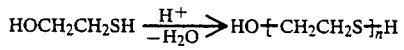

Other U.V.-light stabilizing polyorganosulfides within the above general formula may be prepared by a polycondensation reaction between a dimercaptan and a carbonyl compound, e.g. an aldehyde or ketone, according to the procedure of Marvel et al., 72 J.A.C.S. 2106 (1949) or as described in U.S. Pat. No. 3,317,486.

Furthermore, poly(alicycloalkyldisulfides) may be prepared by oxidizing the corresponding dithiol with air according to the procedure of Marvel et al., 79 J.A.C.S. 3089 (1957), or with a stoichiometric amount of iodine, bromine, or ferric chloride in the presence of base and a suitable solvent, such as benzene.

A wide variety of benzophenones and aromatic acid esters that are known to stabilize polyolefin resins against photodegradation may be used in carrying out the present invention.

As used in the present description and in the appended claims, the term "benzophenone having U.V.-light stabilizing activity" is defined as a compound of the general formula:

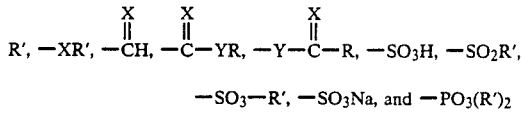

wherein A is independently selected from the group consisting of hydrogen, hydroxyl, halogen, cyano, nitro, $$R', -XR', -\overset{X}{\underset{\|}{C}}H, -\overset{X}{\underset{\|}{C}}-YR, -Y-\overset{X}{\underset{\|}{C}}-R, -SO_3H, -SO_2R',$$

$$-SO_3-R', -SO_3Na, \text{ and } -PO_3(R')_2$$

and R' is alkyl having 1 to 30 carbon atoms, alkenyl having 2 to 20 carbon atoms, cycloalkyl having 3 to 20 carbon atoms, cycloalkylalkyl having 4 to 20 carbon atoms, aryl having 6 to 20 carbon atoms or alkaryl having 7 to 20 carbon atoms, X is independently selected from oxygen or sulfur and Y is independently selected from oxygen, sulfur, $-NR-$, or $-NH-$.

Benzophenones of the above general formula are disclosed in U.S. Pat. Nos. 4,369,228; 4,301,267; 4,169,089; 4,132,704; 4,120,846; 4,116,928; 3,686,367; 3,538,048; 3,415,875; 3,389,004; 3,313,866; 2,904,529; and 2,861,053. Representative examples of suitable benzophenones for use in the present invention are: 2-hydroxy-4-n-octoxybenzophenone, 2-hydroxy-4-n-dodecylbenzophenone, 2,4-dihydroxybenzophenone, 2-hydroxy-4-methoxybenzophenone, 2-hydroxy-4-methoxy- 4'-methylbenzophenone, 2-hydroxy-4-ethoxybenzophenone, 2-hydroxy-4-(2-hydroxyethoxy)benzophenone, 2-hydroxy-4-n-butoxybenzophenone, 2-hydroxy-4-n-hexoxybenzophenone, 2,2'-dihydroxy-4-n-octoxybenzophenone, 2-hydroxy-4-methoxy-4'-carboxybenzophenone, 2-hydroxy-4-chloro-benzophenone, 2,2'-dihydroxy-4,4'-dimethoxybenzophenone, 2,2',4,4'-tetrahydroxybenzophenone, 2-hydroxy-4-methoxy-5-sulfobenzophenone and 2,2'-dihydroxy-4,4'-dimethoxy-5,5'-disulphobenzophenone (disodium salt). The substituent numbers of the foregoing benzophenones correspond to the position numbers of the above general formula.

As used in the present description and in the appended claims, the expression "aromatic acid ester having U.V.-light stabilizing activity" is defined as a compound of the following general formula:

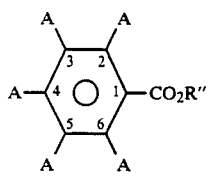

wherein A is as previously defined and R" is a hydrocarbon group having 1 through 30 carbon atoms and is optionally substituted by A. Aromatic acid esters of the above general formula are described in U.S. Pat. Nos. 4,342,875; 4,159,985; 4,066,614; 4,041,011; 4,020,041; and 2,980,648.

Representative examples of suitable aromatic acid esters for use in the present invention are: 2,4-di-t-butylphenyl 3,4-di-t-butyl-4-hydroxybenzoate, n-hexadecyl 3,5-di-t-butyl-4-hydroxybenzoate, 4-octylphenyl 2-hydroxybenzoate, phenyl 2-hydroxybenzoate, 4-butylphenyl 2-hydroxybenzoate, propyl 3,4,5-trihydroxybenzoate, di-4-octylphenyl terephthalate and di-4-nonylphenyl terephthalate. The substituent numbers of the foregoing aromatic acid esters correspond to the position numbers of the above general formula.

The compositions and methods of the present invention are effective for stabilizing a wide variety of polyolefin resins against deterioration caused by exposure to actinic radiation. As used in this description and in the appended claims, the term "polyolefin" is intended to include any normally solid polymer derived from the polymerization of a mono-α-olefinic aliphatic and aryl-substituted aliphatic hydrocarbon having 2 through 20 carbon atoms, and copolymers thereof. This definition is intended also to include polymers of diolefins, as well as olefin/diolefin copolymers. The aforesaid polymeric materials may contain vinyl monomers or substituted vinyl monomers, such as acrylonitrile, styrene, vinyl halide, vinylidene halide, vinyl acetate and the like. Specific examples of the polymers and copolymers which can be rendered stable to actinic radiation in accordance with the present invention are polyethylene, polypropylene, polyisobutylene, poly-2-methylpentene, poly-4-methylpentene, poly-2-methylbutene, polyisoprene, polybutadiene, ethylene-mono-olefin copolymers wherein the mono-olefin has 3 to 20 carbon atoms, propylene-isobutylene copolymers, stryene-butadiene copolymers, styrene-isoprene copolymers, ethylene-vinyl acetate copolymers, vinylidene fluoride-ethylene copolymers, and acrylonitrile-butadiene-styrene terpolymers.

The stabilizer composition of the present invention can be used over a range of about 0.05 to about 10.0 parts by weight per 100 parts of resin. The preferred range is from about 0.1 to about 5.0 parts by weight per 100 parts of resin.

The components of the stabilizer composition itself are generally combined in a weight ratio of 10 through 99.9 weight percent of organosulfide and 0.1 through 90 weight percent of benzophenone or aromatic acid ester. Of course, the relative proportions of components required in any given composition for optimum effectiveness in U.V.-light stabilization will normally depend on the particular organosulfide and benzophenone or aromatic ester used, and may easily be determined by trial. Good results have been obtained using compositions comprising from 60 to 70 weight percent organosulfide and from 30 to 40 weight percent benzophenone or aromatic acid ester.

The compositions of this invention can be incorporated into the polymer resin by any of several well known procedures which provide for uniform distribution in the polymer, such as milling on heated rolls. It has been found effective to mix the stabilizer into the resin by milling the materials on a two-roll mill at 200° C. The polyolefin resin containing the above light stabilizer compositions can then be extruded, injection molded, blow molded, or compression molded into useful articles, such as film, fibers, pipes, or bottles.

These novel light stabilizer compositions can be used as the sole stabilizer or in combination with other conventional light stabilizers such as hindered amines, e.g. bis(2,2,6,6-tetramethyl-4-piperidinyl)sebacate; benzotriazoles, e.g. 2(2'-hydroxyl-5-methylphenyl) benzotriazole; and nickel compounds, e.g. nickel dibutyl dithiocarbamate. Primary and secondary antioxidants such as hindered phenols, e.g. pentaerythritol tetrakis (3,5-di-t-butyl-4-hydroxyhydrocinnamate); phosphites, e.g. distearyl pentaerythritol diphosphite; and organic amines, e.g. N,N'-diphenyl-p-phenylenediamine can be used in combination with the novel stabilizer compositions of this invention.

Other conventional polymer additives such as processing aids, antiblocking and slip agents, biocides, flame retardants, smoke suppressants, coupling and wetting agents, pigments (titanium dioxide, carbon black, and many others), and fillers and/or reinforcements (mica, clay, talc, organic fibers, carbon/graphite fibers, and many others) can also be used in combination with the stabilizers of this invention.

The following examples further describe the manner and process of making and using the present invention and set forth the best mode contemplated for carrying out the invention but are not to be construed as limiting the invention.

Examples 1 through 7 describe the preparation of specific organosulfides useful in the practice of this invention. Examples 1 through 6 also include test results showing the effectiveness of the organosulfides as U.V.-light stabilizers for polyolefin resins. In the examples, all amounts given in parts are parts by weight, unless otherwise indicated.

EXAMPLE 1

Preparation of beta (n-octadecylthio) ethyl-3 and 4-(n-octadecylthio) cyclohexane.

A stirred mixture of 176 g. (1 mole) of beta-mercaptoethyl-3 and 4-mercaptocyclohexane (prepared as a mixture of isomers and not separated) and 560 g. (2 moles) of 1-octadecene under a blanket of nitrogen was heated to 80° C. To this mixture 1.5 g. of 2,2'-azobis(isobutyronitrile) dispersed in 25 g. (0.08 moles) of 1-octadecene was added in four equal portions over a four hour period. The addition of the first portion of the 2,2'-azobis(isobutyronitrile) was accompanied by an exotherm to 110° C. The reaction was held at 80° C. for another four hours, and then 755 g. of hexanes was added. This solution was then cooled to 4° C. and the product (an isomeric mixture) was collected by filtration, washed with 378 g. of cold hexanes, and air dried to yield 516 g (68%) of product. Anal. Calcd. for $C_{44}H_{88}S_2$: C, 77.80; H, 12.76; S,9.44. Found C,77.7; H,12.7; S, 9.25.

A resin composition was made up of 100 parts of polypropylene (Profax 6501, Hercules), 0.05 parts pentaerythritol tetrakis [3,5-di-t-butyl-4-hydroxyhydrocinnamate]cinnamate], 0.05 parts calcium stearate, and 0.3 parts of the organosulfide of this example. The composition was mixed with methylene chloride to form a slurry and the solvent was removed therefrom under vacuum on a rotary evaporator. The resulting material was extruded in a one inch laboratory extruder (temperature profile: Zone 1=190° C., Zone 2=200° C., Zone 3=210° C.) through a six inch sheet die (temperature 215° C.). The 2 mil film was taken up on a Univex Extruder Take Off with a roll temperature of 18° C.

The film was cut into a first set 0.5×5 inch test specimens which were exposed in an Atlas Model Ci35 Weather-Ometer at a black panel temperature of 63°±3° C. Periodically, several specimens were removed for a determination of tensile strength. This determination was based on the time required for the test specimens to reach 50% of the initial tensile strength, referred to herein as "hours to failure" or "HTF". The first set of test specimens had an average HTF value of 400.

Six additional sets of test specimens were prepared in the manner described above, but using different types and/or amounts of U.V.-light stabilizing agent, as indicated in Table I below. The average HTF value for these sets of specimens is also set forth in Table I.

TABLE I

| Set No. | Stabilizing Agent (parts) | Hours to Failure |
|---|---|---|
| 2 | Product of Example 1 (0.3) UV-1 (0.3) | 650 |
| 3 | Product of Example 1 (0.6) | 425 |
| 4 | Product of Example 1 (0.6) UV-1 (0.3) | 850 |
| 5 | Product of Example 1 (0.3) UV-1 (0.15) | 475 |
| 6 | Product of Example 1 (0.3) UV-2 (0.3) | 1300 |
| 7 | Product of Example 1 (0.3) UV-2 (0.3) | 1300 |

UV-1 = 2-hydroxy-4-n-octoxybenzophenone
UV-2 = 2,4-di-t-butylphenyl 3,5-di-t-butyl-4 hydroxybenzoate

EXAMPLE 2

Preparation of 2,9-bis(n-octadecylthio)-p-menthane.

The procedure used was essentially the same as described in Example 1. A stirred mixture of 305 g. (1.498 moles) of 2,9-dimercapta-p-menthane and 786.8 g. (3.05 moles) of 1-octadecene were reacted at 80° C. in the presence of 1.25 g. of 2,2'azobis(isobutyronitrile). The reaction mixture was recrystallized from 1093 g. of hexanes, collected by filtration, washed with 546 g. of cold hexanes, and air dried to give 540 g. (49%) of product. Anal. Calcd. for $C_{46}H_{92}S_2$: C, 77.9; H, 13.1; S, 9.0 Found: C, 78.2; H, 12.9; S, 8.92

Five sets of test specimens incorporating the organosulfide of this example were prepared according to the procedure described above in Example 1. The types and relative amounts of light stabilizing agents used in these sets of specimens and average HTF value for each set of test specimens are set forth in Table II.

TABLE II

| Set No. | Stabilizing Agent (parts) | Hours to Failure |
|---|---|---|
| 8 | Product of Example 2 (0.3) | 375 |
| 9 | Product of Example 2 (0.3) UV-1 (0.3) | 725 |
| 10 | Product of Example 2 (0.6) | 475 |
| 11 | Product of Example 2 (0.6) UV-1 (0.3) | 775 |
| 12 | Product of Example 2 (0.3) UV-1 (0.15) | 475 |

EXAMPLE 3

Preparation of 3,3'-bis(n-octadecylthio)propylether.

A solution of 74.4 g. (0.447 moles) of 3,3'-dithiopropylether and 225.6 g. (0.894 moles) of 1-octadecene in 1.2 liters of hexanes was maintained at 50°–60° C. and irradiated with a 200-watt Hanovia lamp for 4.5 hours. The solvent was stripped and the residue was washed with ether and vacuum dried to give 198.5 g. (66.2%) of crude product. One recrystallization from methyl ethyl ketone gave 186 g. (62%) of the purified product. Anal. Calcd. for $C_{42}H_{86}OS_2$: C, 75.2; H, 12.9; S, 9.6 Found: C, 75.0; H, 12.8; S, 9.6.

Five sets of test specimens were prepared as described above in Example 1, incorporating the organosulfide of this example. The types and relative amounts of light stabilizing agents used in these sets of specimens and the average HTF value for each set of test specimens are given in Table III.

TABLE III

| Set No. | Stabilizing Agent (parts) | Hours to Failure |
|---|---|---|
| 13 | Product of Example 3 (0.4) | 375 |
| 14 | Product of Example 3 (0.3) UV-1 (0.3) | 625 |
| 15 | Product of Example 3 (0.6) | 375 |
| 16 | Product of Example 3 (0.6) UV-1 (0.3) | 650 |
| 17 | Product of Example 3 (0.3) UV-1 (0.15) | 475 |

EXAMPLE 4

Preparation of 1,4 (or 5), 8 (or 9)-tris(n-hexadecylthio) cyclododecane.

The preparation method used was essentially the same as described in Example 1. A stirred mixture of 48.8 g. (0.185 moles) of 1,4 (or 5), 8 (or 9)-trimercaptocyclododecane (prepared as a mixture of isomers and not separated) and 137 g. (0.609 moles) of 1-hexadecene were reacted at 80° C. in the presence of 0.4 g. of 2,2'-azobis(isobutyronitrile). The reaction mixture was recrystallized three times from hexanes (3 × 200 g.) and gave 34 g. of the purified product (an isomeric mixture). Anal. Calcd. for $C_{60}H_{120}S_3$: C, 76.8; H, 12.9; S, 10.3 Found: C, 76.7; H, 12.5; S, 10.2.

Four sets of test specimens incorporating the organosulfide of this example were prepared according to the procedure described above in Example 1. The types and relative amounts of light stabilizing agents used in these sets of specimens and the average HTF value for each set of test specimens is set forth in Table IV.

TABLE IV

| Set No. | Stabilizing Agent (parts) | Hours to Failure |
|---|---|---|
| 18 | Product of Example 4 (0.3) | 425 |
| 19 | Product of Example 4 (0.3) UV-1 (0.3) | 725 |
| 20 | Product of Example 4 (0.6) | 475 |
| 21 | Product of Example 4 (0.6) UV-1 (0.3) | 950 |

EXAMPLE 5

Preparation of Poly-2-mercaptoethanol.

A mixture of 50 g. (0.41 moles) of 2-mercaptoethanol, 0.5 g. of sulfuric acid and 300 ml. of toluene were brought to reflux in a three-necked flask equipped with a Dean-Stark trap. After six hours of reflux, 11 g. of a mixture of 2-mercaptoethanol and water was removed from the Dean-Stark trap. Filtration of the hot reaction mixture yielded a white solid which was washed first with 100 ml. of toluene, then with 100 ml. of saturated $NaHCO_3$ solution, and finally with 100 ml. of distilled water. After drying under a hard vacuum at 100° C. the yield of the product was 14 g. Anal. Calcd. for $(C_2H_4S)_n$: C, 40.0: H, 6.71; S, 53.3 Found: C, 40.4: H, 6.76; S, 50.2.

Four sets of test specimens incorporating the organosulfide of this example were prepared according to the procedure of Example 1. The types and relative amounts of light stabilizing agents in these sets of specimens and the average HTF value of each set of test specimens is set forth in Table V.

TABLE V

| Set No. | Stabilizing Agent (parts) | Hours to Failure |
|---|---|---|
| 22 | Product of Example 5 (0.3) | 350 |
| 23 | Product of Example 5 (0.3) UV-1 (0.3) | 750 |
| 24 | Product of Example 5 (0.6) | 350 |
| 25 | Product of Example 5 (0.6) UV-1 (0.3) | 750 |

EXAMPLE 6

Preparation of 1,4-bis(n-octadecylthio)butane.

The procedure used was essentially the same as described in Example 1. A stirred mixture of 12.22 g. (0.1 moles) of 1,4-butane dithiol and 50.5 g. (0.2 moles) of 1-octadecene were reacted at 80° C. in the presence of 0.5 g. of 2,2'-azobis(isobutyronitrile). The reaction mixture was recrystallized twice from hexanes (2×300 g.) collected by filtration, washed with 100 g. of cold hexanes, and air dried to yield 45.5 g. of pure product. Anal. Calcd. for $C_{40}H_{82}S_2$: C, 76.6; H, 13.2; S, 10.2 Found: C, 76.2; H, 12.9: S, 10.2.

Two sets of test specimens containing the organosulfide of this example were prepared according to the procedure described above in Example 1. The types and relative amounts of light stabilizing agents in these sets of specimens and the average HTF value of each set of test specimens are given in Table VI.

TABLE VI

| Set No. | Stabilizing Agent (parts) | Hours to Failure |
|---|---|---|
| 26 | Product of Example 6 (0.6) | 425 |
| 27 | Product of Example 6 (0.6) UV-1 (0.3) | 700 |

Several additional test specimens were made and the HTF values thereof determined, as described above in Example 1, to provide a basis for comparison in evaluating the HTF values reported in Examples 1 through 6. A control containing no U.V.-light stabilizing agent of any kind had an average HTF value of 325; test specimens containing 0.3 parts and 0.6 parts, respectively, of distearyl thiodipropionate (DSTDP) as the sole light stabilizing agent had an average HTF value of 325; test specimens containing 0.3 parts U.V.-1 and 0.3 parts DSTDP had an average HTF value of 500; test specimens containing 0.3 parts U.V.-1 and 0.6 parts DSTDP had an average HTF value of 450; test specimens containing 0.3 parts of UV-1 as the sole light stabilizer had an average HTF value of 500; and test specimens containing 0.3 parts of UV-2 as the sole light stabilizer had an average HTF value of 1100.

EXAMPLE 7

Preparation of beta-mercaptoethyl -3 and 4-mercaptocyclohexane polymer with formaldehyde and octylthiol.

A mixture of 76 g. (0.52 moles) of beta-mercaptoethyl-3 and 4-mercaptocyclohexane and 11.7 g. (0.38 moles) of para-formaldehyde were stirred under a blanket of nitrogen for sixteen hours at 22° C. The mixture was heated to 65° C. for one-half hour and then cooled to room temperature. To this mixture 23 g. (0.16 moles) of 1-octylthiol, 90 g. of hexanes, and 0.1 g. (0.001 moles) of methane sulfonic acid were added and the reaction mixture was brought to reflux in a three-necked flask equipped with a Dean-Stark trap. After three hours of reflux, 6.2 g. of water was collected in the Dean-Stark trap. The solution was then cooled to room temperature, washed twice with 100 ml. of ten percent sodium hydroxide solution, and dried over magnesium sulfate. The solvent was removed under vacuum yielding 93 g. of a light amber liquid with no mercaptan odor and an average molecular weight of 1368.

The foregoing examples show that the organosulfides of this invention can generally be prepared in reasonably high yields. The reactions employed do not require specialized apparatus or extreme conditions. The examples further show that the organosulfides of this invention exhibit significant activity as U.V.-light stabilizers for polyolefins, and produce a synergistic U.V.-light stabilizing effect with benzophenone and aromatic acid ester U.V.-light stabilizers.

While certain presently preferred embodiments of the present invention have been described and exemplified hereinabove, it is not intended to limit the invention to such embodiments, but various modifications may be made therein and thereto without departing from the spirit and scope of the invention as set forth in the following claims.

What is claimed is:

1. A method for stabilizing polyolefin resin against degradation by UV-light which comprises incorporating in said polyolefin resin a UV-light stabilizing composition comprising:
   (1) a synergizing effective amount of an organosulfide for UV-light stabilization, said organosulfide having the general formula:

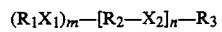

$(R_1X_1)_m-[R_2-X_2]_n-R_3$ wherein $R_1$ and $R_3$ may be the same or different and are independently selected from the group of hydrogen, alkyl having 1 to 30 carbon atoms, cycloalkyl having 3 to 20 carbon atoms, cycloalkylalkyl having 4 to 20 carbon atoms, and aryl having 6 to 20 carbon atoms, which radicals may optionally be substituted with substituents from the group of halogen or —YR, wherein Y is either oxygen or sulfur and R is a hydrocarbon radical from the group of alkyl having 1 to 20 carbon atoms, alkenyl having 2 to 20 carbon atoms, cycloalkyl having 3 to 20 carbon atoms, aryl having 6 to 20 carbon atoms, or alkaryl having 7 to 20 carbon atoms;

m represents a number from 1 to 10;

$R_2$ represents a linking group selected from the group of straight or branched, saturated or unsaturated, aliphatic having 2 to 20 carbon atoms, an alicyclic having 3 to 20 carbon atoms, alicyclicalkyl having 4 to 20 carbon atoms, or aromatic having 6 to 20 carbon atoms or a plurality of said linking groups, which may be the same or different, and which are joined by oxygen or sulfur, provided that when $R_2$ is aliphatic no two sulfur atoms are attached to the same $R_2$ carbon atom;

$X_1$ and $X_2$ represent oxygen or sulfur, at least one of said $X_1$ and $X_2$ being sulfur; and n is a number from 1 to 1,000, provided that when $R_2$ is aliphatic having 5 or less carbon atoms n must equal 1; and (2) a benzophenone having UV-light stabilizing activity or an aromatic acid ester having UV-light stabilizing activity, or mixtures thereof.

2. A method according to claim 1 wherein said UV-light stabilizing composition comprises, by weight, from about 10 percent to 99.9 percent of said organosulfide compound and from about 0.1 percent to about 90 percent of said benzophenone, aromatic acid ester, or mixtures thereof.

3. A method according to claim 1 wherein said UV-light stabilizing composition comprises, by weight, from about 60 percent to about 70 percent of said organosulfide compound and from about 30 percent to about 40 percent of said benzophenone, aromatic acid ester, or mixtures thereof.

4. A method according to claim 1 wherein the organosulfide is selected from the group of beta(n-octadecylthio)ethyl-3-(n-octadecylthio)cyclohexane, beta(n-octadecylthio)ethyl-4-(n-octadecylthio)cyclohexane, or an isomeric mixture thereof, and the UV-light stabilizing compound is 2-hydroxy-4-n-octoxybenzophenone.

5. A method according to claim 1 wherein the organosulfide is 2,9-bis(n-octadecylthio)-p-methane and the UV-light stabilizing compound is 2-hydroxy-4-n-octoxybenzophenone.

6. A method according to claim 1 wherein the organosulfide is 3,3'-bis(n-octadecylthio)propyl ether and the UV-light stabilizing compound is 2-hydroxy-4-n-octoxybenzophenone.

7. A method according to claim 1 wherein the organosulfide is selected from the group of 1,4,8-tris(n-hexadecylthio)cyclododecane, 1,5,9-tris(n-hexadecylthio)cyclododecane, or an isomeric mixture thereof and the UV-light stabilizing compound is 2-hydroxy-4-n-octoxybenzophenone.

8. A method according to claim 1 wherein the organosulfide is 1,4-bis(n-octadecylthio)butane and the UV-light stabilizing compound is 2-hydroxy-4-n-octoxybenzophenone.

9. A method according to claim 1 wherein the organosulfide compound is beta(n-octadecylthio)ethyl-3-(n-octadecylthio)cyclohexane, or an isomeric mixture thereof, and the UV-light stabilizing compound is 2,4-di-t-butylphenyl 3,5-di-t-butyl-4-hydroxybenzoate.

10. A method according to claim 1 wherein the polyolefin resin is selected from the group of polyethylene, polypropylene, polyisobutylene, poly-2-methyl-pentene, poly-4-methylpentane, poly-2-methylbutene, polyisoprene, polybutadiene, ethylene-mono-olefin copolymers wherein the mono-olefin has 3 to 20 carbon atoms, propylene-isobutylene copolymers, styrene-butadiene copolymers, styrene-isoprene copolymers, ethylene-vinyl acetate copolymers, vinylidene fluoride-ethylene copolymers, and acrylonitrile-butadiene-styrene terpolymers.

11. A method according to claim 10 wherein the polyolefin is selected from the group consisting of polyethylene, polypropylene or copolymers thereof.

12. A method according to claim 1 wherein the UV-light stabilizing composition is incorporated in the polyolefin in an amount from 0.05 to about 10.0 parts of the UV-light stabilizing composition per 100 parts of polyolefin, by weight.

13. A method according to claim 12 wherein the UV-light stabilizing composition is incorporated in the polyolefin in an amount from 0.1 to about 5.0 parts of the UV-light stabilizing composition per 100 parts of polyolefin, by weight.

14. A method according to claim 1, wherein $R_1$ and $R_3$ in the general formula may be the same or different and are independently selected from the group of hydrogen or alkyl having 8 to 30 carbon atoms;
m represents a number from 1 to 5;
$R_2$ represents a linking group selected from the group of alicyclic having 5 to 15 carbon atoms or alicyclicalkyl having 5 to 15 carbon atoms;
$X_1$ and $X_2$ represent sulfur;
and n is 1.

15. A method according to claim 14 wherein said UV-light stabilizing benzophenone is 2-hydroxy-4-n-octoxy-benzophenone.

16. A method according to claim 14 wherein said UV-light stabilizing aromatic acid ester is 2,4-di-t-butylphenyl 3,5-di-t-butyl-4-hydroxylbenzoate.

17. A composition comprising:
(a) a UV-light stabilizing composition comprising:
(1) a synergizing effective amount of an organosulfide for UV-light stabilization, said organosulfide having the general formula:

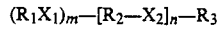

wherein $R_1$ and $R_3$ may be the same or different and are independently selected from the group of hydrogen, alkyl having 1 to 30 carbon atoms, cycloalkyl having 3 to 20 carbon atoms, cycloalkylalkyl having 4 to 20 carbon atoms, and aryl having 6 to 20 carbon atoms, which radicals may optionally be substituted with substitutes from the group of halogen or —YR, wherein Y is either oxygen or sulfur and R is a hydrocarbon radical from the group of alkyl having 1 to 20 carbon atoms, alkenyl having 2 to 20 carbon atoms, cycloalkyl having 3 to 20 carbon atoms, aryl having 6 to 20 carbon atoms, or alkaryl having 7 to 20 carbon atoms;
m represents a number from 1 to 10;
$R_2$ represents a linking group selected from the group of straight or branched, saturated or unsaturated, aliphatic having 2 to 20 carbon atoms, an alicyclic having 3 to 20 carbon atoms, alicyclicalkyl having 4 to 20 carbon atoms, or aromatic having 6 to 20 carbon atoms or a plurality of said linking groups, which may be the same or different, and which are joined by oxygen or sulfur, provided that when $R_2$ is aliphatic no two sulfur atoms are attached to the same $R_2$ carbon atom;
$X_1$ and $X_2$ represent oxygen or sulfur, at least one of said $X_1$ and $X_2$ being sulfur; and
n is a number from 1 to 1,000, provided that when $R_2$ is aliphatic having 5 or less carbon atoms n must equal 1; and
(2) a benzophenone having UV-light stabilizing activity or an aromatic acid ester having UV-light stabilizing activity, or mixtures thereof; and
(b) polyolefin resin.

18. A composition according to claim 17 wherein said UV-light stabilizing composition comprises, by weight, from about 10 percent to 99.9 percent of said organosulfide compound and from about 0.1 percent to about 90 percent of said benzophenone, aromatic acid ester, or mixtures thereof.

19. A composition according to claim 17 wherein said UV-light stabilizing composition comprises, by weight, from about 60 percent to 70 percent of said organosulfide compound and from about 30 percent to about 40 percent of said benzophenone, aromatic acid ester, or mixtures thereof.

20. A composition according to claim 17 wherein the organosulfide is selected from the group of beta(n- octadecylthio)ethyl-3-(n-octadecylthio)cyclohexane, beta(n-octadecylthio)ethyl-4-(n-octadecylthio)cyclohexane, or an isomeric mixture thereof, and the UV-light stabilizing compound is 2-hydroxy-4-n-octoxybenzophenone.

21. A composition according to claim 17 wherein the organosulfide is 2,9-bis(n-octadecylthio)-p-menthane and the UV-light stabilizing compound is 2-hydroxy-4-n-octoxybenzophenone.

22. A composition according to claim 17 wherein the organosulfide is 3,3'-bis(n-octadecylthio)propyl ether and the UV-light stabilizing compound is 2-hydroxy-4-n-octoxybenzophenone.

23. A composition according to claim 17 wherein the organosulfide is selected from the group of 1,4,8-tris(n-hexadecylthio)cyclododecane, 1,5,9-tris(n-hexadecylthio)cyclododecane, or an isomeric mixture thereof and the UV-light stabilizing compound is 2-hydroxy-4-n-octoxybenzophenone.

24. A composition according to claim 17 wherein the organosulfide is 1,4-bis(n-octadecylthio)butane and the UV-light stabilizing compound is 2-hydroxy-4-n-octoxybenzophenone.

25. A composition according to claim 17 wherein the organosulfide compound is beta(n-octadecylthio)ethyl-3-(n-octadecylthio)cyclohexane, or an isomeric mixture thereof, and the UV-light stabilizing compound is 2,4-di-t-butylphenyl 3,5-di-t-butyl-4-hydroxybenzoate.

26. A composition according to claim 17 wherein the polyolefin resin is selected from the group of polyethylene, polypropylene, polyisobutylene, poly-2-methylpentene, poly-4-methylpentene, poly-2-methylbutene, polyisoprene, polybutadiene, ethylene-mono-olefin copolymers wherein the mono-olefin has 3 to 20 carbon atoms, propylene-isobutylene copolymers, styrene-butadiene copolymers, styrene-isoprene copolymers, ethylene-vinyl acetate copolymers, vinylidene fluoride-ethylene copolymers, and acrylonitrile-butadiene-styrene terpolymers.

27. A composition according to claim 26 wherein the polyolefin is selected from the group consisting of polyethylene, polypropylene or copolymers thereof.

28. A composition according to claim 17 wherein the UV-light stabilizing composition is incorporated in the polyolefin in an amount from 0.05 to about 10.0 parts of the UV-light stabilizing composition per 100 parts of polyolefin, by weight.

29. A composition according to claim 28 wherein the UV-light stabilizing composition is incorporated in the polyolefin in an amount from 0.1 to about 5.0 parts of the UV-light stabilizing composition per 100 parts of polyolefin, by weight.

30. A composition according to claim 17 wherein $R_1$ and $R_3$ in the general formula may be the same or different and are independently selected from the group of hydrogen or alkyl having 8 to 30 carbon atoms;

m represents a number from 1 to 5;

$R_2$ represents a linking group selected from the group of alicyclic having 5 to 15 carbon atoms or alicyclicalkyl having 5 to 15 carbon atoms;

$X_1$ and $X_2$ represent sulfur;

and n is 1.

31. A composition according to claim 30 wherein said UV-light stabilizing benzophenone is 2-hydroxy-4-n-octoxybenzophenone.

32. A composition according to claim 30 wherein said UV-light stabilizing aromatic acid ester is 2,4-di-t-butylphenyl 3,5-di-t-butyl-4-hydroxylbenzoate.

* * * * *